United States Patent
Brand et al.

(10) Patent No.: US 6,255,514 B1
(45) Date of Patent: Jul. 3, 2001

(54) ISOLATION OF TRIMETHOXYSILANE FROM A TMS/METHANOL MIXTURE

(75) Inventors: Alexandra Brand, Darmstadt; Hans-Josef Sterzel, Dannstadt-Schauernheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/677,863

(22) Filed: Oct. 3, 2000

(30) Foreign Application Priority Data

Oct. 4, 1999 (DE) ................................. 199 47 591

(51) Int. Cl.⁷ ................................. C07F 7/08; C07F 7/18
(52) U.S. Cl. ............................. 556/470; 556/466
(58) Field of Search ..................... 556/466, 470

(56) References Cited

U.S. PATENT DOCUMENTS 5,166,384 * 11/1992 Bailey et al. ..................... 556/466
5,804,040 * 9/1998 Asai et al. ..................... 556/466 X
6,090,965 * 7/2000 Lewis et al. ..................... 556/470
6,166,237 * 12/2000 Simandan et al. ............... 556/470

FOREIGN PATENT DOCUMENTS

| 310 920 | 4/1989 | (EP) . |
| 462 359 | 12/1991 | (EP) . |
| 6-252488 | 12/1985 | (JP) . |

\* cited by examiner

*Primary Examiner*—Paul F. Shaver
(74) *Attorney, Agent, or Firm*—Keil & Weinkauf

(57) ABSTRACT

In an extraction process for isolating trimethoxysilane (TMS) from a TMS/methanol mixture by formation of two phases, namely a TMS-rich extract phase and a methanol-rich raffinate phase, by addition of one or more methanol-soluble inorganic and/or organic salts and, if desired, an additional nonpolar organic solvent and subsequent phase separation, the amount of salt added is selected so that the weight ratio of trimethoxysilane to methanol in the extract phase is at least 94% by weight:6% by weight (normalized to 100% by weight). The use of one or more inorganic salts in an extraction process for isolating trimethoxysilane from a trimethoxysilane/methanol mixture is also claimed.

8 Claims, No Drawings

ISOLATION OF TRIMETHOXYSILANE FROM A TMS/METHANOL MIXTURE

The invention relates to a process for isolating trimethoxysilane (TMS) from a TMS/methanol mixture.

TMS is customarily prepared by direct synthesis from silicon metal and methanol. In this process, TMS is obtained in the form of TMS/methanol mixtures. These mixtures cannot be worked up by simple distillation because the two components TMS and methanol form an azeotrope. The TMS/methanol azeotrope consists of 55% by weight of TMS and 45% by weight of methanol and boils at 62.5° C., while methanol has a boiling point of 64.5° C. and TMS has a boiling point of 84° C.

Processes for working up TMS/methanol mixtures are known from the prior art. In these, the TMS/methanol mixture is separated by means of extractive distillation with the aid of azeotrope breakers such as n-hexane, n-heptane or organic solvents in general which have a dipole moment of <1.61 D and form an azeotrope with methanol. The fact that the azeotrope breakers form an azeotrope with methanol makes these processes disadvantageous, since the recovery and reuse of the individual components methanol and the azeotrope breaker is very complicated and thus uneconomical.

EP-A 0 310 920 discloses a process for separating TMS from a TMS/methanol mixture by extractive distillation. In this process, high-boiling tetramethoxysilane (TTMS), which is unreactive and does not form an azeotrope with either of the components of the mixture, is used as extractant. Extraction occurs because of the greater affinity of TTMS for TMS than for methanol. However, a good separation requires a 3- to 10-fold excess of TTMS which has to be prepared separately, which means that the costs of this process are high.

EP-A 0 462 359 relates to a process for working up a TMS/methanol mixture without addition of further substances. In this process, the TMS/methanol azeotrope obtained is returned to the synthesis reactor for the direct synthesis of TMS from silicon metal and methanol and only the amount of TMS above the azeotrope ratio of TMS to methanol is isolated.

All the abovementioned processes have the disadvantage that the TMS/methanol mixture has to be brought to elevated temperatures without prior removal of the methanol, as a result of which the undesirable subsequent reaction of TMS with methanol to give tetramethoxysilane (TTMS) is accelerated and the yield of TMS is therefore reduced.

JP 60/252488 (as Derwent Abstract No. 86-031969/05) relates to the extraction of TMS from a TMS/methanol mixture using organic solvents and/or organopolysiloxanes which are immiscible with the TMS/methanol mixture but are miscible with the TMS. An inorganic or organic salt can be added for salting-out, so as to improve the effectiveness of the extraction. The best TMS/methanol ratios achieved in the extract phase (=uptake phase, essentially solvent and desired product, here TMS) are 93.7% by weight of TMS:6.3% by weight of methanol.

According to K. Sattler, "Thermische Trennverfahren", second revised and expanded edition, VCH-Verlagsgesellschaft mbH, Weinheim, 1995, pages 498 ff, liquid-phase extraction does not lead, in contrast to other possibly competing separation processes such as distillation, directly to the individual, separated components of the mixture, but instead an additional separation step is necessary. This is because the raffinate phase (=release phase, consisting essentially of a carrier material, here methanol) comprises not only the carrier material but also residues of solvents which may have to be separated off. The extract phase (=uptake phase, essentially solvent and desired product, here TMS) consists essentially of solvents and desired product and therefore has to be separated into the solvent to be returned to the extraction step and the desired product in an additional separation step. This increased complexity of an extraction compared to a distillation is only economical when very good separation of the components of the mixture is achieved, i.e. when a solvent having a high selectivity is used.

A critical factor for carrying out the extraction process for separating TMS and methanol is therefore the discovery of a suitable solvent or a suitable way of achieving a high separation efficiency. The choice of an optimum solvent for the extraction makes it possible to achieve cost savings and thus good economics of the extraction process.

It is an object of the present invention to provide an economical process for isolating TMS from a TMS/methanol mixture, in which process TMS can be obtained in good yields without thermal stressing of the TMS/methanol mixture.

The achievement of this object starts out from an extraction process for isolating TMS from a TMS/methanol mixture by formation of two phases, namely a TMS-rich extract phase and a methanol-rich raffinate phase, by addition of one or more methanol-soluble inorganic and/or organic salts and, if desired, an additional nonpolar organic solvent and subsequent phase separation.

In the process of the present invention, the amount of salt added is selected so that the weight ratio of TMS to methanol in the extract phase is at least 94% by weight (TMS):6% by weight (methanol) (normalized to 100% by weight).

The use of the optimum extractant enables very good separation efficiencies to be achieved, as a result of which TMS can be isolated in pure form in high yields. The process of the present invention makes it possible to isolate TMS gently without thermal stressing of the TMS/methanol mixture, so that the formation of by-products is low.

For the purposes of the present invention, an extraction process is a process in which a separation of the TMS/methanol mixture to form two phases, namely a TMS-rich phase (extract phase) and a methanol-rich phase (raffinate phase), is carried out. In this process, the addition of a nonpolar solvent is possible but not absolutely necessary.

The higher the ratio of TMS to methanol in the extract phase, the higher the yield of TMS. The ratio of TMS to methanol is therefore preferably $\geq 96\%$ by weight:$\leq 3\%$ by weight, particularly preferably $\geq 98\%$ by weight:$\leq 2\%$ by weight.

The amount of salt which is optimum in terms of separation efficiency and economics depends, inter alia, on whether additional nonpolar solvent is added and, if so, which nonpolar solvent is added. When additional nonpolar solvent is added, the amount of salt, based on the amount of TMS and methanol, is preferably at least 0.5% by weight, particularly preferably from 0.5 to <10% by weight, very particularly preferably from 7 to <10% by weight.

If a nonpolar solvent is used, it serves, together with the salt used, as phase former to form two phases, namely the extract phase consisting essentially of TMS and the nonpolar solvent and the raffinate phase consisting essentially of methanol and salt.

As nonpolar solvents which can be used if desired, preference is given to using nonpolar solvents which are immiscible with the TMS/methanol mixture but are miscible with TMS. Suitable solvents are preferably selected from the group consisting of branched and unbranched $C_8$–$C_{16}$-alkanes and mixtures thereof, fluorinated hydrocarbons, diphenylalkanes, dialkylbenzenes and linear alkylbenzenes. Particular preference is given to dodecane and $C_{12-14}$-alkane mixtures.

Any nonpolar solvent added is generally added in a ratio of nonpolar solvent to TMS and methanol of 10-0.5:1, preferably 5-1:1. In a very particularly preferred embodiment of the process of the present invention, no nonpolar solvent is added as extractant.

This embodiment has the advantage that only few components participate in the isolation of the TMS from the TMS/methanol mixture. If the extraction process is followed by purification of the product by distillation, in which large amounts of the nonpolar solvent usually have to be heated so as to separate it off, which is associated with high energy consumption, this embodiment of the present invention requires a significantly lower energy input since no nonpolar solvent has to be separated off. Furthermore, contamination of the TMS by solvent residues is prevented.

In the process of the present invention, it is possible to use both organic and inorganic salts. Suitable inorganic salts are, for example, halides, perchlorates, tetrafluoroborates, sulfates and nitrates, and suitable organic salts are acetates and carboxylates. Cations used can be cations of the metals of groups 1 and 2 of the Periodic Table of the Elements and of iron (in its divalent and trivalent forms as salt) and zinc and also the ammonium ion. Preference is given to using one or more salts selected from the group consisting of halides, perchlorates, tetrafluoroborates, acetates and carboxylates of metals of groups 1 and 2 of the Periodic Table of the Elements, of iron (in its divalent or trivalent form as salt), zinc and of the ammonium ion. Particular preference is given to sodium chloride, lithium chloride, calcium chloride, iron(II) chloride and zinc(II) chloride. Very particular preference is given to lithium chloride, which is inexpensive and leads to very good phase separations. Furthermore, among all the particularly preferred salts, lithium chloride has the greatest solubility in methanol.

The extraction process of the present invention can be carried out in one or more stages. For example, the following variants can be employed:
(a) single-stage extraction, including differential batchwise with recirculated solvent,
(b) multistage extraction in cross-current,
(c) multistage extraction in countercurrent,
(d) multistage extraction in countercurrent with extract recirculation.
(a) In single-stage extraction, the mixture of methanol and TMS to be treated is intensively mixed once with addition of the salt and, if desired, with all the solvent in the mixing zone of an extraction apparatus. After the distribution equilibrium has been approximately or fully established in the separation zone of the extraction apparatus, extract phase and raffinate phase leave the separation zone of the extraction apparatus. The extract phase consists essentially of TMS and any solvent added, but usually still contains residual methanol. The raffinate phase is composed of methanol and possibly residues of solvents and TMS and also the salt used. In differential batchwise extraction, the mixture is initially mixed well with the salt and, if desired, solvent in a vessel. After extraction has occurred, a raffinate phase and an extract phase are obtained and the latter is continually taken off. The solvent, if used, present in the extract phase is continually recirculated and thus effects better extraction of the TMS from the mixture.
(b) Multistage extraction in cross-current of raffinate phase (release phase) and extract phase (uptake phase) can be carried out continuously or batchwise. In continuous cross-current extraction, the TMS/methanol mixture flows to a first stage where it is treated with salt and, if desired, solvent. The extraction which occurs leads to a raffinate stream and an extract stream. The raffinate phase is passed on from stage to stage and in each case admixed with fresh or regenerated extract phase, while the extract phase is taken off from each stage and is usually combined for work-up. In batchwise extraction, the same process can be carried out in an extraction apparatus with stirrer. From a local series of extraction stages, a time sequence of mixing and thus extraction steps and settling phases with the respective extract phase being taken off and, in each case, mixing with fresh uptake phase into the remaining raffinate phases is now carried out.
(c) In countercurrent extraction, the TMS/methanol mixture to be treated or the raffinate phase (release phase) and the extract phase (uptake phase) are passed in countercurrent through a plurality of extraction vessels (mixer-settlers) connected in series or through extraction columns. The mixture and the extract phase (uptake phase) flow toward the opposite ends of the multistage extractor, so that the raffinate stream, if desired with fresh solvent, and the extract stream are in contact with the feed mixture to be treated (TMS/methanol mixture). This leads to high concentration differences for the transfer component (TMS) between the inflowing and outflowing phases and thus to good enrichment of the extract phase with the transfer component and to substantial removal of this component from the raffinate phase.
(d) The concentration of TMS in the extract phase leaving the extractor which can be achieved in countercurrent extraction can be increased further by recirculation of worked-up extract phase to the column. This occurs in countercurrent extraction with extract recirculation.

The extraction process of the present invention is preferably carried out by multistage extraction in cross-current (b) or in countercurrent with recirculation of the extract phase (d).

Apparatuses suitable for the extraction process are, for example, columns with internals such as random packing, ordered packing, sieve trays and stirred cells so as to achieve very high phase turbulence and a high mass transfer area and thus good exchange of transfer component (TMS) between the phases.

Examples of suitable extraction apparatuses are:
static columns (column with random packing, sieve tray column, column with ordered packing),
pulsed columns (column with random packing, sieve tray column, Karr column),
stirred columns (rotating disk contactor (RDC), asymmetric rotating disk contactor (ARD), QVF stirred cell extractor, Kühni extractor, etc.),
mixer-settlers or a mixer-settler battery and tower mixer-settlers.

Preference is given to extraction apparatuses which have a low susceptibility to salt encrustations, i.e. columns with energy input, for example pulsed columns, in particular pulsed packed columns, and stirred columns.

Further information on liquid—liquid extraction processes and on extraction apparatuses may be found, for example, in K. Sattler, "Thermische Trennverfahren", second revised and expanded edition, VCH Verlagsgesellschaft mbH, Weinheim, 1995, pages 507–566.

The process of the present invention is generally carried out at $\leq 65°$ C., preferably from −40 to +60° C., particularly preferably from −20 to +40° C. The extraction can generally be carried out at any pressure. It is usually carried out at atmospheric pressure.

The present invention further provides for the use of one or more inorganic or organic salts in an extraction process for isolating TMS from a TMS/methanol mixture in accordance with the process of the present invention.

The following examples illustrate the invention.

EXAMPLES

Example C1 (Comparative Example, without Salt)

A mixture of 20 g of trimethoxysilane and 15.2 g of methanol is extracted with 176 g of dodecane in a shaking funnel at room temperature. For this purpose, the mixture is shaken briefly 50 times. After three minutes, the procedure is repeated. The compositions of the solvent phase and the raffinate are determined by analysis by means of gas chromatography. Table 1 summarizes the relevant distribution (K) and extraction (E) coefficients.

TABLE 1

| Phase | Weight [g] | Without salt | % by weight | | | |
|---|---|---|---|---|---|---|
| | | | MeOH | TMS | TTMS | Dodecane |
| Upper | 196.4 | | 2.87 | 7.96 | 0.31 | 88.86 |
| Lower | 13.3 | 13.3 | 51.32 | 21.49 | 5.22 | 21.87 |

Weight ratio of TMS to MeOH in the extract phase, normalized to 100% by weight:73.5% by weight:26.5% by weight.

Example 2 (with Solvent)

A mixture of 20 g of trimethoxysilane, 15.2 g of methanol and 3 g of lithium chloride are extracted with 35.2 g of dodecane in a shaking funnel at room temperature. For this purpose, the mixture is shaken briefly 50 times. After three minutes, the procedure is repeated. The compositions of the solvent phase and the raffinate are determined by analysis by means of gas chromatography. To determine the lithium chloride content, the two phases are evaporated on a rotary evaporator. Lithium chloride is found quantitatively in the methanol phase. Table 2 summarizes the relevant distribution (K) and extraction (E) coefficients.

TABLE 2

| Phase | Weight [g] | Without salt | % by weight | | | |
|---|---|---|---|---|---|---|
| | | | MeOH | TMS | TTMS | Dodecane |
| Upper | 57.4 | | 0.01 | 30.92 | 6.75 | 62.32 |
| Lower | 17.3 | 14.3 | 70.3 | 17.94 | 10.95 | 0.80 |

Weight ratio of TMS to MeOH in the extract phase, normalized to 100% by weight:99.97% by weight:0.03% by weight.

Example 3 (without Solvent)

A mixture of 20 g of trimethoxysilane (96.4%), 15.2 g of methanol and 4.1 g of lithium chloride is mixed in a shaking funnel at room temperature. The mixture is shaken briefly 50 times. After three minutes, the procedure is repeated. Phase separation takes place after about one minute. The compositions of the trimethoxysilane phase and the methanol phase are determined by analysis by means of gas chromatography. The two phases are evaporated on a rotary evaporator to determine lithium chloride. Lithium chloride is found quantitatively in the methanol phase. Table 3 summarizes the results.

TABLE 3

| Phase | Weight [g] | Without salt | Normalized % | | | Content [g] | | |
|---|---|---|---|---|---|---|---|---|
| | | | MeOH | TMS | TTMS | MeOH | TMS | TTMS |
| Upper | 14.3 | 14.3 | 2.55 | 95.1 | 2.36 | 0.36 | 13.6 | 0.34 |
| Lower | 24.2 | 20.1 | 79.72 | 15.26 | 5.01 | 16.02 | 3.07 | 1.01 |

Weight ratio of TMS to MeOH in the extract phase, normalized to 100% by weight:97.4% by weight:2.6% by weight.

We claim:

1. An extraction process for isolating trimethoxysilane (TMS) from a TMS/methanol mixture by formation of two phases, namely a TMS-rich extract phase and a methanol-rich raffinate phase, by addition of one or more methanol-soluble inorganic and/or organic salts and, if desired, an additional nonpolar organic solvent and subsequent phase separation, wherein the amount of salt added is selected so that the weight ratio of trimethoxysilane to methanol in the extract phase is at least 94% by weight:6% by weight (normalized to 100% by weight).

2. A process as claimed in claim 1, wherein nonpolar solvents selected from the group consisting of branched and unbranched $C_8$–$C_{16}$-alkanes, fluorinated hydrocarbons, diphenylalkanes, dialkylbenzenes and linear alkylbenzenes are added.

3. A process as claimed in claim 1, wherein no additional nonpolar solvent is added.

4. A process as claimed in claim 1, wherein one or more salts selected from the group consisting of halides, perchlorates, tetrafluoroborates, acetates and carboxylates of metals of groups 1 and 2 of the Periodic Table of the Elements, iron (in its divalent or trivalent form), zinc and the ammonium ion is/are added.

5. A process as claimed in claim 4, wherein lithium chloride is added.

6. A process as claimed in claim 1, wherein the extraction process is carried out in a plurality of stages or continuously.

7. A process as claimed in claim 1, wherein the extraction process is carried out as a multistage extraction in cross-current or as a multistage extraction in countercurrent.

8. A process as claimed in claim 1, wherein the temperature is $\leq 65°$ C.

* * * * *